United States Patent
Gupta et al.

(10) Patent No.: US 10,342,844 B2
(45) Date of Patent: Jul. 9, 2019

(54) ANTI-PROLIFERATIVE EFFECTS OF PALM VEGETATION LIQUOR AND EXTRACTS THEREOF IN PREVENTING PANCREATIC CANCER

(71) Applicant: MALAYSIAN PALM OIL BOARD, Kajang, Selangor (MY)

(72) Inventors: Smiti V. Gupta, Oakland Township, MI (US); Pramod Khosla, Troy, MI (US); Xiangming Ji, Detroit, MI (US); Ravigadevi Sambanthamurthi, Selangor (MY); Yew Ai Tan, Selangor (MY)

(73) Assignee: Malaysian Palm Oil Board, Kajang (MY)

( * ) Notice: Subject to any disclaimer, the term of this patent is extended or adjusted under 35 U.S.C. 154(b) by 41 days.

(21) Appl. No.: 15/400,556

(22) Filed: Jan. 6, 2017

(65) Prior Publication Data

US 2017/0151304 A1    Jun. 1, 2017

Related U.S. Application Data

(62) Division of application No. 14/651,972, filed as application No. PCT/MY2013/000228 on Dec. 3, 2013, now abandoned.

(30) Foreign Application Priority Data

Dec. 13, 2012    (MY) .................. PI/2012/701146

(51) Int. Cl.
| | |
|---|---|
| A61K 36/00 | (2006.01) |
| A61K 36/889 | (2006.01) |
| A61K 45/06 | (2006.01) |
| A61K 31/05 | (2006.01) |
| A23L 33/105 | (2016.01) |
| A61K 9/00 | (2006.01) |

(52) U.S. Cl.
CPC .......... *A61K 36/889* (2013.01); *A23L 33/105* (2016.08); *A61K 9/0053* (2013.01); *A61K 31/05* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 7,425,548 B2 | 9/2008 | Nair et al. |
| 2006/0057237 A1 | 3/2006 | Darro et al. |
| 2009/0004302 A1 | 1/2009 | Cyr |
| 2010/0197780 A1 | 8/2010 | Manickam et al. |
| 2010/0278943 A1 | 11/2010 | Sambanthamurthi et al. |
| 2011/0293753 A1 | 12/2011 | Bellafiore et al. |

FOREIGN PATENT DOCUMENTS

| | | |
|---|---|---|
| WO | 2009146102 A1 | 12/2009 |
| WO | 2014/092532 A1 | 6/2014 |

OTHER PUBLICATIONS

Prasad, Grape proanthocyanidin inhibit pancreatic cancer cell growth in vitro and in vivo through induction of apoptosis and by targeting the PI3K/Akt pathway. PloS one, (2012) vol. 7, No. 8, pp. e43064.*
Schwarz, Pancreatic cancer in vitro toxicity mediated by Chinese herbs SPES and PC-SPES: implications for monotherapy and combination treatment. Cancer letters, (Jan. 10, 2003) vol. 189, No. 1, pp. 59-68.*
Hafeez et al, Plumbagin, a plant derived natural agent inhibits the growth of pancreatic cancer cells in in vitro and in vivo via targeting EGFR, Stat3 and NF-.kappa.B signaling pathways. International journal of cancer, (Nov. 1, 2012) vol. 131, No. 9, pp. 2175-2186.*
S. D. Sekaran et al., "Effects of oil palm phenolics on tumor cells in vitro and in vivo", African Journal of Food Science, 2010, vol. 4, No. 8, pp. 495-502.
A. Berger et al., "Scutellaria baicalensis extract and constituent flavonoids inhibit proliferation in pancreatic cancer cell lines", Gastroenterology, 2006, vol. 130, No. 4, Suppl. 2, pp. A118-A119.
A. B. Kunnumakkara et al., "γ-Tocotrienol Inhibits Pancreatic Tumors and Sensitizes Them to Gemcitabine Treatment by Modulating the Inflammatory Microenvironment", Cancer Research, 2010, vol. 70, No. 21, pp. 8695-8705.

* cited by examiner

*Primary Examiner* — Qiuwen Mi
(74) *Attorney, Agent, or Firm* — Melissa M. Hayworth; E. Joseph Gess

(57) ABSTRACT

Present invention relates to a composition to inhibit cancer cell proliferation, wherein said composition comprises oil palm extracts. The composition is useful for prevention of pancreatic cancer by inhibiting clonogenicity, inducing apoptosis, regulating gene expression, inducing anti-invasive effect, and induces cell cycle arrest in S phase. Present invention also discloses a composition that inhibits NF-κB activity and reduces cell invasion, cell migration and metastasis. Present invention further discloses the use of therapeutically effective amount of a composition in inhibiting the growth of pancreatic cancer.

19 Claims, 4 Drawing Sheets

Specification includes a Sequence Listing.

ANTI-PROLIFERATIVE EFFECTS OF PALM VEGETATION LIQUOR AND EXTRACTS THEREOF IN PREVENTING PANCREATIC CANCER

CROSS-REFERENCE TO RELATED APPLICATIONS

This application is a divisional of U.S. application Ser. No. 14/651,972 filed on Jun. 12, 2015, which is a National Stage Application of International Application No. PCT/MY2013/000228 filed on Dec. 3, 2013, which claims benefit of Malaysian Serial No. PI 2012701146, filed Dec. 13, 2012 in Malaysia, and which applications are incorporated herein by reference in their entireties. To the extent appropriate, a claim of priority is made to each of the above disclosed applications.

FIELD OF THE INVENTION

The present invention relates to a composition of anti-proliferative effects in cancer. More particularly, relates to a palm-based composition that includes but is not limited to phenolic compounds for use in preventing pancreatic cancer.

BACKGROUND OF THE INVENTION

The oil palm fruit (*Elaeis guineensis*) contains large amounts of lipid or water soluble bioactive agents such as vitamin E (tocopherols, tocotrienols), carotenoids and phytosterols. The lipid-soluble tocotrienols are shown to have anti-tumor effects on human cancer cells like prostate, breast, colon, melanoma, and lung cancers. Water-soluble oil palm phenolics (OPP) have been demonstrated to show potential anticancer properties. Sambanthamurthi et al (2011) showed that phenolics inhibit tumour progression in tumour-inoculated mice; however there is no disclosure on tumour growth inhibition in pancreatic cancer using palm vegetation liquor. Sekaran et al (2010) have demonstrated that OPP can inhibit proliferation and induce apoptosis in different cancer cell lines such as breast, lung, and skin cancers in vitro. It was also found that OPP reduces tumor growth in vivo. However, there is no study available to disclose the effect of oil palm bioactive agents on pancreatic cancer cell growth. Therefore, it is an object of present invention to utilize the extract from this oil palm vegetation liquor in treating pancreatic cancer (PaCa).

Pancreatic cancer (PaCa) is one of the leading causes of cancer death with poor survival rate due to its aggressiveness and early metastases. Despite more focused research in this area recently, the mortality rate for PaCa has remained fairly high. The common treatments for PaCa patients are pancreatectomy, or surgical resection of the organ, followed by chemo, targeted and/or radiotherapies.

Gemcitabine is a purine analog which is used as a standard clinical chemotherapeutic agent for advanced PaCa treatment; however this agent has shown a poor tumor response rate with short survival time. Erlotinib is a targeting epidermal growth factor receptor tyrosine kinase which is used as an adjuvant to gemcitabine by inhibiting cell growth signaling but again showing marginally improved survival benefits in clinical trials.

Detrimental side effects of these chemotherapeutic agents available targeting PaCa such as heart attack, stroke and death have been documented. This results in limited advantage due to their dose limiting toxicity to normal tissues. Thus, it is an object of present invention to provide an alternative to enhance chemotherapeutic activity for pancreatic cancer with minimal adverse effects.

Another object of present invention is to curb the adverse effects and chemoresistance suffered by most gemcitabine-treated patients. It becomes crucial to develop a novel therapeutic agent in order to improve prognosis with natural plant extracts.

It is yet another object of present invention to provide a bioactive dietary agent used in combination with drug to achieve the pleiotropic effects which lessen the toxicity and dose requirements of therapeutics alone.

The nuclear factor κB (NF-κB) is widely used as a regulator of genes that control cell proliferation and cell survival, and it plays important roles in cancer cell transformation, cell invasion, and apoptosis. P65 is a subunit of NF-κB that interacts with promoter sequence of target genes which in turn induces the expression of genes involving in inflammatory, anti-apoptosis, and proliferation. This signaling pathway has been targeted as a strategy for anti-cancer therapy in PaCa patients. NF-κB is a common and constitutively expressed transcription factor which is activated through a wide variety of stimuli such as inflammation and oxidative stress. On stimulation, NF-κB is translocated to the nucleus and binds to the promoters of its target genes to begin transcription of specific genes. Overexpression of NF-κB may results in apoptosis resistance, angiogenesis, migration and invasion of cancer cells.

Studies have shown that NF-κB is constitutively activated in approximately 67% of pancreatic adenocarcinomas compared to normal pancreatic tissue, and this is associated with aggressive stage pancreatic cancer and drug resistance. Based on the role of NF-κB in regulating carcinogenic activity in pancreatic cancer and the anti-inflammatory behavior of palm vegetation liquor, present invention serves the purpose to describe the effect of palm vegetation liquor in pancreatic cancer cell model, characterized in the potential down-regulation of the NF-κB pathway.

Thus, it is yet another object of present invention to provide a composition for anti-proliferation in pancreatic cancer via regulation of NF-κB pathway.

It is a further object of the present invention to provide an improved composition and method based on compounds extracted from vegetation liquor i.e. aqueous stream of the palm oil milling process for providing inhibitory effect against pancreatic cancer.

Accordingly, present invention also relates to an extraction process of bioactives from the oil palm vegetation liquor from the milling process. The processing of oil palm produces large amounts of vegetation liquor rich in phenolic compounds, shikimic acid, fruit acids, fruit sugars and glycerol which can be further enriched using conventional membrane filtration technology.

Further objects and advantages of the present invention may become apparent upon referring to the preferred embodiments of the present invention as shown in the accompanying drawings and as described in the following description.

SUMMARY OF THE INVENTION

The invention relates to a composition to inhibit cancer cell proliferation, wherein said composition comprises oil palm phenolics derived from oil palm extracts and vegetation liquor. The composition is useful for prevention of pancreatic cancer from PANC-1 and BxPC-3 cell lines by inhibiting clonogenicity, inducing apoptosis, regulating gene expression, anti-invasive effect, and induces cell cycle arrest in S phase.

The apoptosis is associated with inducing caspase, inhibiting cell survival proteins and inhibiting anti-apoptotic protein. The anti-apoptotic protein disclosed herein is Survivin. The composition also down-regulates Bcl-XL gene expression which is from Bcl-2 family.

The composition induces apoptosis by increasing expression of pro-apoptotic proteins such as cleaved caspase 3, caspase 9 or Poly (ADP-ribose) polymerase (PARP).

Present invention also discloses a composition that inhibits NF-κB activity via down-regulating p65 subunit activity. Vascular endothelial growth factor (VEGF) and matrix metalloproteinase 9 (MMP9) gene expressions are down-regulated to reduce cell invasion, cell migration and metastasis. The composition may be provided as compounds with pharmaceutically acceptable carriers.

Present invention further discloses the use of therapeutically effective amount of a composition in the preparation of a medicament for preventing or inhibiting the growth of pancreatic cancer in an individual by administering to an individual in need thereof. The composition is accompanied with or without conventional chemotherapy or radiation therapy or surgery, or it may be administered orally or as a food supplement.

BRIEF DESCRIPTION OF THE DRAWINGS

These and other features, aspects, and advantages of the present invention will become better understood with regard to the following description, appended claims, and accompanying drawings, in which:

DETAILED DESCRIPTION OF THE INVENTION

Figure 1:
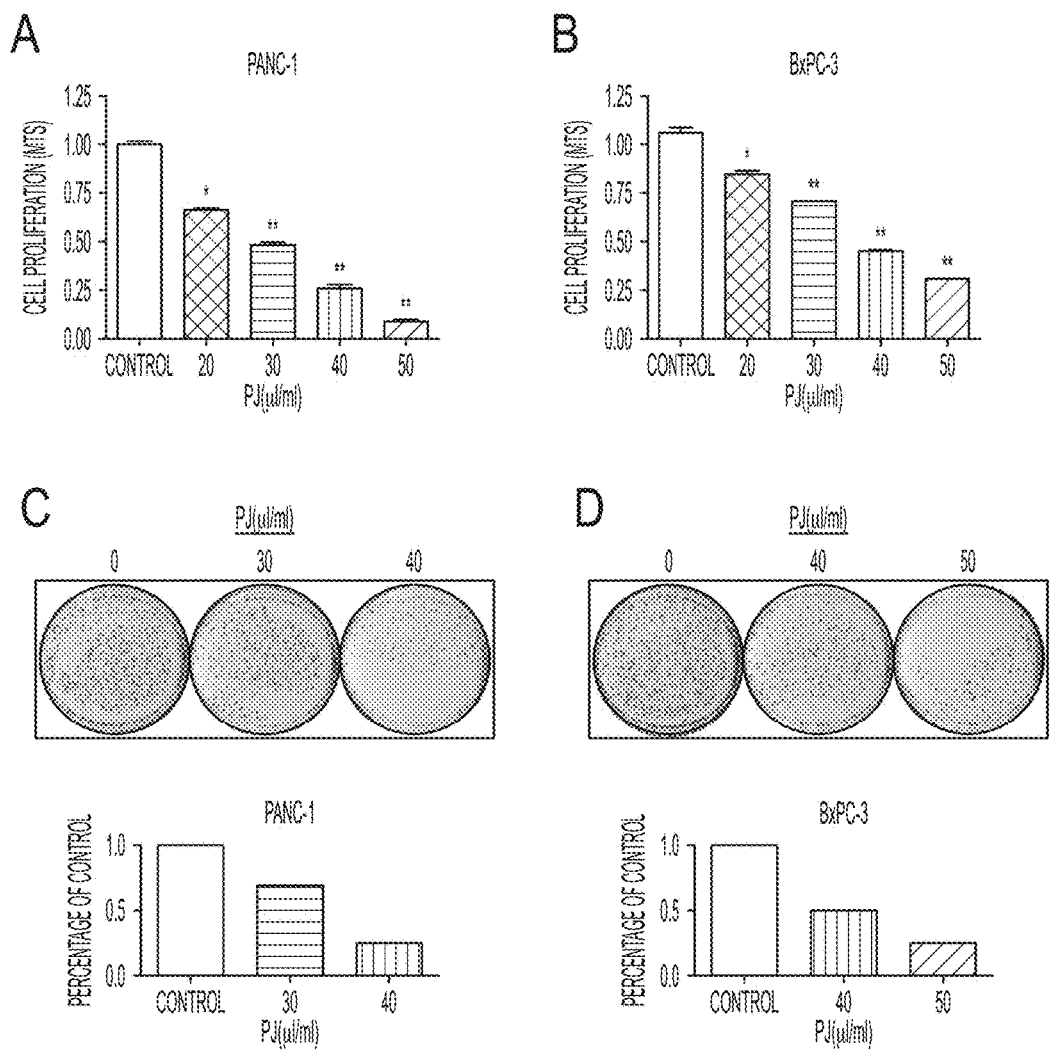
FIG. 1 shows the effect of phenolic-rich extract from oil palm vegetation liquor designated palm juice (PJ) on pancreatic cancer cell line PANC-1 and BxPC-3 survival and growth (A and B) and clonogenicity (C and D)

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Present invention provides palm juice (PJ) which constitutes a water soluble phenolic-rich extract from the palm fruit (*Elaeis guineensis*) and/or its vegetation liquor and has documented high antioxidant, anti-inflammatory, and anti-carcinogenic activity in breast cancer cells.

Present invention also discloses anti-tumor effects of the phenolic-rich extract by treating two pancreatic cancer cell lines (PANC-1 and BxPC-3) with different doses of palm juice (PJ). PJ was observed to induce anti-proliferative, apoptotic and anti-invasive effects using the (3-(4,5-dimethylthiazol-2-yl)-5-(3-carboxymethoxyphenyl)-2-(4-sulfophenyl)-2H-tetrazolium) (MTS) assay, cytoplasmic histone-DNA fragment quantification and matrigel invasive assays in a dose dependent manner. Real-time PCR has confirmed the anti-invasive effects induced by PJ through a decrease in the gene expressions of MMP-9 and VEGF. Flow cytometer is used to demonstrate that cells arrest in S phase in cell cycle analysis. Western blot analysis has also been conducted to show that apoptosis induced by PJ was associated with down regulation of expression in Survivin and Bcl-XL gene and up regulation of expression in cleaved caspase 3, caspase 9 and PARP gene. These results demonstrate the anti-tumor activity of PJ in pancreatic cancer cells, providing initial evidence towards its potential therapeutic uses.

BEST MODE FOR CARRYING OUT THE INVENTION

The method of preparation and use of the present invention is further illustrated by the following experimental examples. It should be understood that these experimental examples, while indicating preferred embodiments of the invention, are given by way for better elucidation only. A person skilled in the art can ascertain the essential characteristics and embodiments of this invention, therefore various changes may be provided to adapt to various usages and conditions.

Materials and Methods

Cell Culture, Reagents and Antibodies:

Human PaCa cell lines, including PANC-1 and BxPC-3 were grown in Dulbecoo's Modified Eagle Medium (DMEM) supplemented with 10% fetal bovine serum (FBS) and 1% penicillin and streptomycin in 5% $CO_2$. Palm juice (PJ) extracted from oil palm was prepared at a stock concentration of 1500 mg/ml GE (gallic acid equivalents). Protease inhibitor cocktail, primary antibodies for Poly (ADP-ribose) polymerase (PARP), β-actin and cell lysis buffer (20 mM Tris-HCl pH 7.5, 150 mM NaCl, 1 mM $Na_2EDTA$, 1 mM EGTA, 1% Triton X-100, 2.5 mM sodium pyrophosphate, 1 mM beta-glycerophosphate, 1 mM $Na_3VO_4$, 1 µg/ml leupeptin), primary antibodies against cleaved caspase 3 and cleaved caspase 9, Survivin, $Bcl-X_L$ and secondary antibodies were obtained from commercially available supply.

Cell Viability Studies by MTS Assay

The PANC-1 and BxPC-3 cells ($5 \times 10^3$) were seeded and incubated overnight in 96-well culture plates. The medium was then removed and replaced with a fresh medium containing 20, 30, 40 or 50 µl of PJ (1500 mg/mL GE) per ml of cell prior to 72 h of incubation. After that, 20 µl of MTS assay reagent was added to each well and incubated for 2 h at 37° C. in a humidified, 5% $CO_2$ atmosphere. The reading was then recorded in absorbance at 490 nm using plate reader. This assay is repeated by replacing PJ with dimethyl sulfoxide (DMSO) as the vehicle control. Each variant of the experiment was performed in triplicate.

Histone/DNA ELISA for Detection of Apoptosis

The Cell Death Detection Enzyme-linked immunosorbent assay (ELISA) Kit was used to detect apoptosis in PaCa cells. One million cells were seeded and incubated overnight in six-well plates before treating with PJ or control for 72 h. The cells were then lysed and the cytoplasmic histone/DNA fragments were extracted and incubated in microtiter plate modules coated with anti-histone antibody. Peroxidase-conjugated anti-DNA antibody were used to detect the immobilized histone/DNA fragment before color development with 2,2'-azino-bis(3-ethylbenzothiazoline-6-sulphonic acid) (ABTS) substrate for peroxidase. The spectrophotometric absorbance of the samples was determined by using plate reader at wavelength of 405 nm.

Clonogenic Assay

One million cells were seeded and incubated overnight in a 100 mm dish. The cells were cultured with 20, 30, 40 or 50 µl of PJ or control for 72 h prior to viable cell counting and plating with about 5,000 cells per plate. The cells were then incubated for 21 days at 37° C. in a 5% $CO_2$ incubator. All the colonies were fixed in 4% paraformaldehyde and stained with 2% crystal violet.

Flow Cytometry and Cell Cycle Analysis

Cells were seeded and incubated overnight in 100 mm dish before subjecting all the cells for starvation for 24 h. The cells were released into control or PJ containing media for 72 h of incubation. Subsequently, cells were collected and fixed with ice-cold 70% (v/v) ethanol for 24 h. After subjecting cells for centrifugation at 3000×g for 5 min, the cell pellet was washed with PBS (pH 7.4) and resuspended in PBS containing propidium iodide (50 µg/mL), and DNase-free RNase (1 µg/mL). Samples were then incubated at room temperature for 2 h, and DNA content was determined using a flow cytometer.

Annexin V-FITC Method for Apoptosis Analysis

Annexin V-Fluorescein isothiocyanate (FITC) apoptosis detection kit was used to measure the apoptotic cells. PANC-1 and BxPC-3 cells were incubated in the presence or absence of PJ for 48 h before subjecting cells for trypsinisation, washing with ice-cold PBS and resuspension in 1× binding buffer at a concentration of $10^5$ cells per ml in a total volume of 100 µl. The cells were then added with 5 µl of Annexin V-FITC and 5 µl of PI (Propidium Iodide) and were kept in the dark for 20 min at room temperature. Finally, each tube was added with 400 µl of 1× binding buffer and the number of apoptotic cells was analyzed using flow cytometer.

Wound Healing Assay

PANC-1 and BxPC-3 were seeded and incubated overnight in a six well plate at a concentration of $4×10^5$ cells per well. After incubation, culture media were removed and a scratch wound across each well was made using fine tips. In order to ensure no loosely held cells were attached near to wound areas, the wound areas were washed three times with PBS. Subsequently, the cells were cultured in presence or absence of PJ and the wound images were taken as 0 h. After 20 h, wound healing pictures were taken under microscope.

Cell Invasive Assay

A biocoat matrigel invasion kit was used to evaluate the tumor invasive ability according to the manufacturer's protocol. Around $5×10^4$ cells of PANC-1 and BxPC-3 with basal media was transferred in each 6-well upper chamber in the presence or absence of PJ, while 3 ml of culture medium with 10% FBS was added into each lower chamber of 24-well plate. The cells in the upper chamber were removed using a cotton stick after 20 h of incubation. Then the cells that invaded through the Matrigel matrix membrane were stained with 4 µg/mL Calcein AM in Hanks buffered saline at 37° C. for 1 h. Each of experimental conditions was performed in triplicates. Subsequently, fluorescence of the invaded cells was read using a microplate reader at excitation/emission wavelengths of 530/590 nm. A fluorescent microscope was used to capture images of these fluorescently labeled invasive cells.

Protein Extraction and Western Blotting

PANC-1 and BxPC-3 cell lines were treated with or without of PJ for 72 h to evaluate the effects of treatment on PARP, cleaved caspase 3, cleaved caspase 9, Survivin, Bcl-$X_L$, and βactin expressions. Cells were lysed in cold lysis buffer for 30 mins on ice and the protein concentrations were determined using a protein assay kit. The samples were loaded on 10% SDS-polyacrylamide gels and subjected to electrophoresis. After electrophoresis, the gel was electrophoretically transferred to a nitrocellulose membrane using transfer buffer (25 mM Tris, 190 mM glycine, 20% methanol) in a transfer apparatus. The membranes were incubated for 1 h at room temperature with 5% nonfat dried milk in 1× tris-buffered saline (TBS) buffer containing 0.1% polysorbate 20 (TBS-T) before incubating overnight at 4° C. with primary antibodies. The membranes were subjected to washing for 3 times with TBS-T and incubated with the secondary antibodies containing 2% bovine serum albumin (BSA) for 2 h at room temperature before measuring signal intensity using a chemiluminescent imager.

Real-Time Quantitative PCR for Gene Expression Analysis

Total RNA was isolated according to the kit manufacturer's protocols. First strand cDNA synthesis was performed on 2 µg of total RNA from each sample using TaqMan reverse transcription reagents kit in a total volume of 20 µl. Reverse transcription reaction were performed at 25° C. for 10 min, followed by 48° C. for 30 min and 95° C. for 5 min. Real-time PCR analysis were performed and sequences of the primers sets used for this analysis are as follows: MMP-9, forward primer (5'-CGG AGT GAG TTG AAC CAG-3') (SEQ ID NO: 1) and reverse primer (5'-GTC CCA GTG GGG ATT TAC-3') (SEQ ID NO: 2); VEGF, forward primer (5 '-GCC TTG CCT TGC TGC TCT AC-3') (SEQ ID NO: 3) and reverse primer (5 '-TTC TGC CCTCCT CCT TCT GC-3') (SEQ ID NO: 4); GAPDH, forward primer (5'-CAG TGA GCT TCC CGT TCAG-3') (SEQ ID NO: 5) and reverse primer (5'-ACC CAG AAG ACT GTG GAT GG-3') (SEQ ID NO: 6).

All these primers were verified by virtual PCR, and primer concentrations were optimized to avoid primer dimer formation. Real-time PCR amplifications were performed using 2×SYBR Green PCR Master Mix. Two microliters of RT reaction were used for a total volume of 25 µl quantitative PCR reactions. The thermal profile for SYBR real-time PCR was 95° C. 10 min followed by 50 cycles of 95° C. 15 s and 60° C. 1 m. Data were analyzed according to the comparative fold increase or decrease in gene expression determined by quantitation of normalized Glyceraldehyde 3-phosphate dehydrogenase (GAPDH) expression in each sample.

Microwell Colorimetric NF-κB Assay

In order to evaluate the binding activity of NF-κB, a transcription factor ELISA kit for P65 was used according to the manufacturer's protocol. One million of PANC-1 and BxPC-3 cells were seeded and incubated overnight in 100 mm dish before treating with PJ or control for 72 h and nuclear protein extraction from each sample. Then, 2 µg of each sample were incubated in microplate coated with anti-p65 DNA sequence. Peroxidase-conjugated anti-DNA antibody was used to detect the p65-DNA binding complex before color development with ARTS substrate for peroxidase. The chemiluminescence and volume of the samples were recorded and analyzed.

Data Analysis

Results are expressed as means±standard error of the mean (SEM) and statistical comparisons between groups were done using one-way ANOVA. Values of p<0.05 were considered to be statistically significant and individual p-values are reported in the figures.

Results

Effects of PJ on Cell Growth/Survival of PaCa Cells

The cytotoxic potential of PJ on pancreatic cancer cell lines was evaluated by treating PANC-1 and BxPC-3 cells with different concentrations of PJ and culture medium followed by the MTS and clonogenic assays as shown in FIG. 1. FIG. 1 shows the effect of PJ on pancreatic cancer cell line PANC-1 and BxPC-3 survival and growth (A and B) and clonogenicity (C and D).

Both cancer cell lines were treated with increasing concentrations of PJ. Results are presented as mean±SEM of three assay replicates. In reference to FIG. 1, * indicates P<0.05 and ** indicates P<0.01 versus respective DMSO treated controls. The number of cells counted in the control treatment was considered 100% and the number of cells in PJ treated cells was calculated in relative to this control.

In PANC-1 cell line, treatment with 20, 30, 40 and 50 µl/ml of PJ for 72 h resulted in 35%, 51%, 75% and 91% of cell growth inhibition in relative to control, respectively. Similarly, treatment on BxPC-3 cell line with 20, 30, 40 and 50 µl/ml of PJ for 72 h resulted in 12%, 30%, 54% and 75% of cell growth inhibition in relative to control respectively. These results indicate that the efficiency of PJ as an inhibitor of pancreatic cancer cell growth.

Clonogenic assay as depicted in FIGS. 1C and 1D confirms the effects of PJ on cell growth by revealing the treatment of PANC-1 and BxPC-3 with increasing concentrations of PJ (30 and 40 µl/ml) resulted in a greater reduction in the number of colonies, as indicated by reduced crystal violet staining. As shown in FIG. 1, the results from the clonogenic assay were consistent with the MTS data where PJ significantly inhibited pancreatic cancer cell growth. Summarizing both assays, it is found that PJ inhibited cell proliferation and clonogenicity in both cell lines where PANC-1 cells were more sensitive to the effects of PJ than BxPC-3 cells for all concentrations tested.

Induction of Apoptosis by PJ

Figure 2:
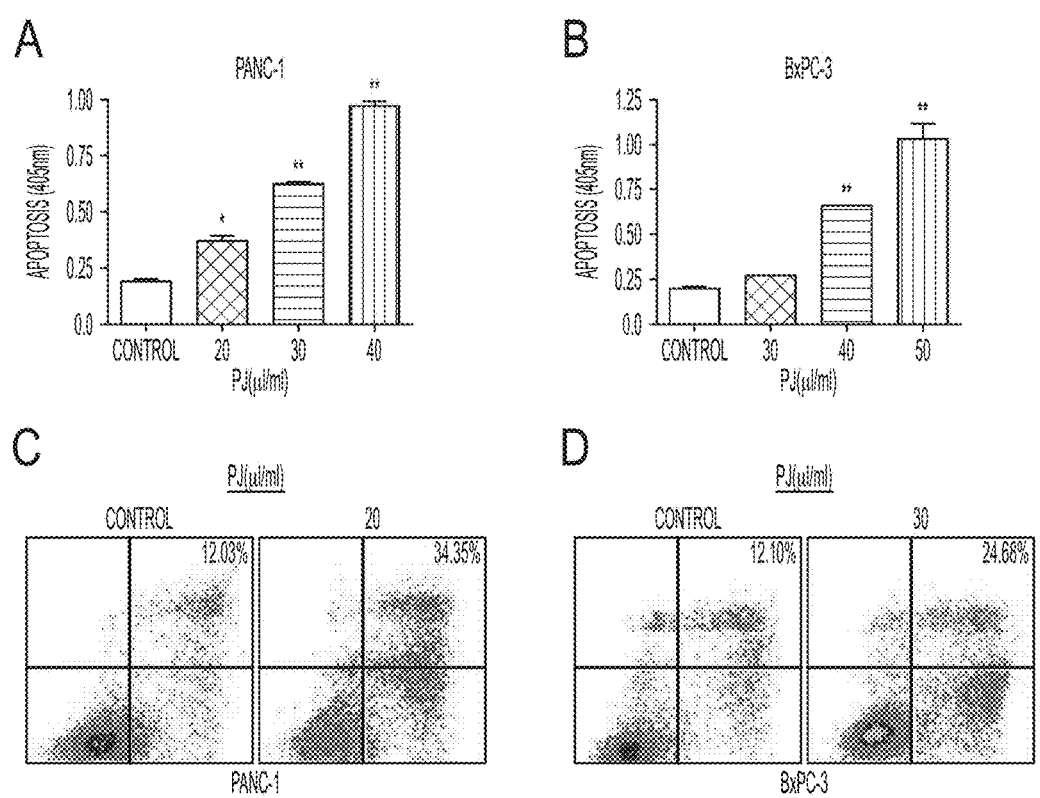
FIG. 2 shows the apoptosis analysis by Histone Kit/DNA ELISA method (A and B) and flow cytometry (C and D)

FIG. 2 depicted the analysis of apoptotic ability of PJ with Histone/DNA ELISA method (A and B) and flow cytometry (C and D). Cells were treated with increasing concentration of PJ or treated with DMSO as vehicle control prior to incubation for 72 h. The incubation is followed by staining with Annexin V and propidium iodide for flow cytometry analysis. The flow cytometric cell distribution of cells is illustrated in dot plots (FIGS. 2C and 2D). The values represent ±SEM of triplicate samples. * indicates P<0.05 and ** indicates P<0.01 versus DMSO-treated control groups.

FIGS. 2A and 2B show PJ induced apoptosis in PANC-1 (FIG. 2A) and BxPC-3 (FIG. 2B) cell lines in a dose dependent manner. FIGS. 2C and 2D indicates quantitation of apoptotic cells, as detected by Annexin V staining after treatment with 20 and 30 µl/ml of PJ, thus confirming the apoptosis-inducing effect of PJ in both cell lines. The result showed that PJ treatment is statistically significant (**P<0.01) increasing in percentage of apoptotic cells in both pancreatic cancer cell lines at $IC_{50}$ dosage of PJ.

Analysis of Cell Cycle Distribution After Treatment with PJ

Figure 3:
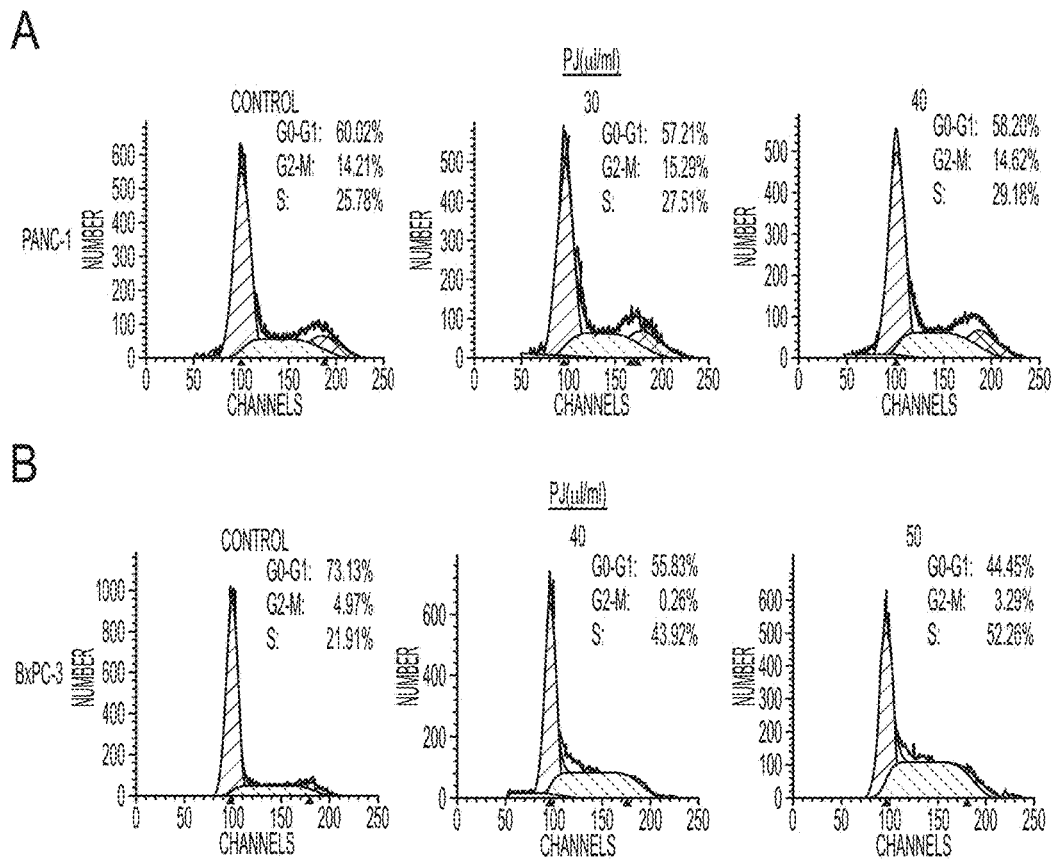
FIG. 3 shows the effect of PJ on gene expression.

The cell cycle distributions of PANC-1 and BxPC-3 cells treated with varying concentrations of PJ were analyzed to determine possible underlying mechanism of cell proliferation suppression as depicted in FIG. 3A (PANC-1) and FIG. 3B (BxPC-3). The distribution of populations in different cell cycle phases was quantified using flow cytometer after 72 h of incubation.

FIGS. 3A and 3B indicate that both cell lines were arrested in the S phase by PJ in a dose-depended manner. For PANC-1 cell (FIG. 3A), about 28% cells are arrested in S phase in treatment group (40 µl/ml) as compared to 25% in control cells. A similar observation was made in BxPC-3 cells (FIG. 3B) with 52% of cells arrested in S phase in treatment group (50 µl/ml) as compared to 21% in control cells.

Cell cycle distribution of cancer cells treated with increasing concentrations of PJ are shown along with the percentages of the cell cycle stages, G0-G1, G2-M, and S phase. These findings reveal that PJ induced cell cycle arrest in the S phase for both cancer cell lines.

PJ Both Up-Regulates Pro-Apoptotic Genes and Down-Regulates Anti-Apoptotic Genes Western blotting represents the expression of PARP cleavage, caspases, Bcl-xL and Survivin in PANC-1 and BxPC-3 cancer cell lines after 72 h of treatment with increasing PJ concentration to further elaborate the molecular mechanisms involve in PJ-induced apoptosis of pancreatic cancer cells. The β-actin protein was utilized as the protein loading control for this experiment.

Figure 4:
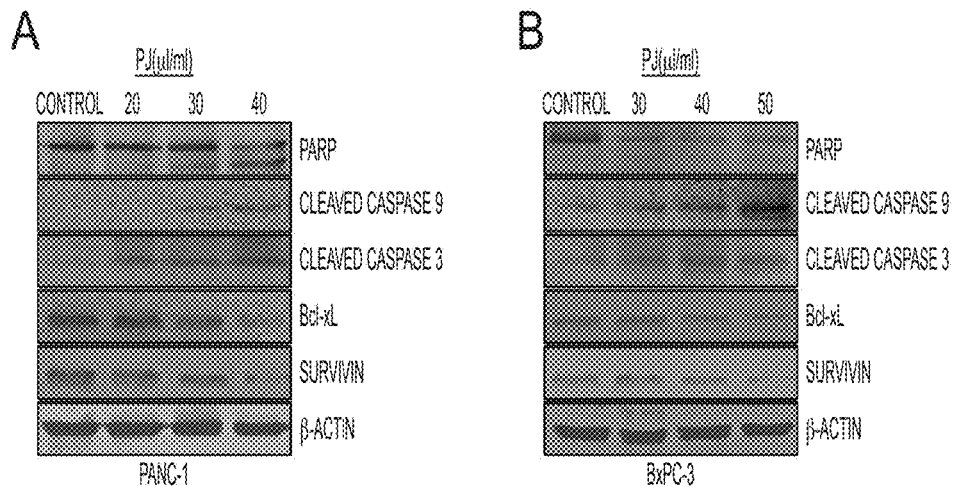
FIG. 4 shows the response of PJ on cell cycle regulation in PANC-1 (A) and BxPC-3 (B) cancer cell lines.

Specifically, the expression of proteins involved in the induction of cleaved caspase dependent apoptosis (caspase 3, caspase 9), anti-apoptotic Bcl-2 family (Bcl-xL) and anti-apoptotic protein—Survivin were analyzed. FIG. 4 illustrates that PJ increases expression of pro-apoptotic proteins, cleaved caspase 3 and 9 and PARP in both cancer cell lines, while decreases production of anti-apoptotic proteins such as Bcl-xL and Survivin in both PANC-1 and BxPC-3 cell lines.

This analysis demonstrates that PJ induces apoptosis in both cancer cell lines through a dual-mechanistic approach: activation of apoptosis inducing caspases and inhibition of cell survival proteins.

Inhibition of NF-κB Activity with PJ

Figure 5:
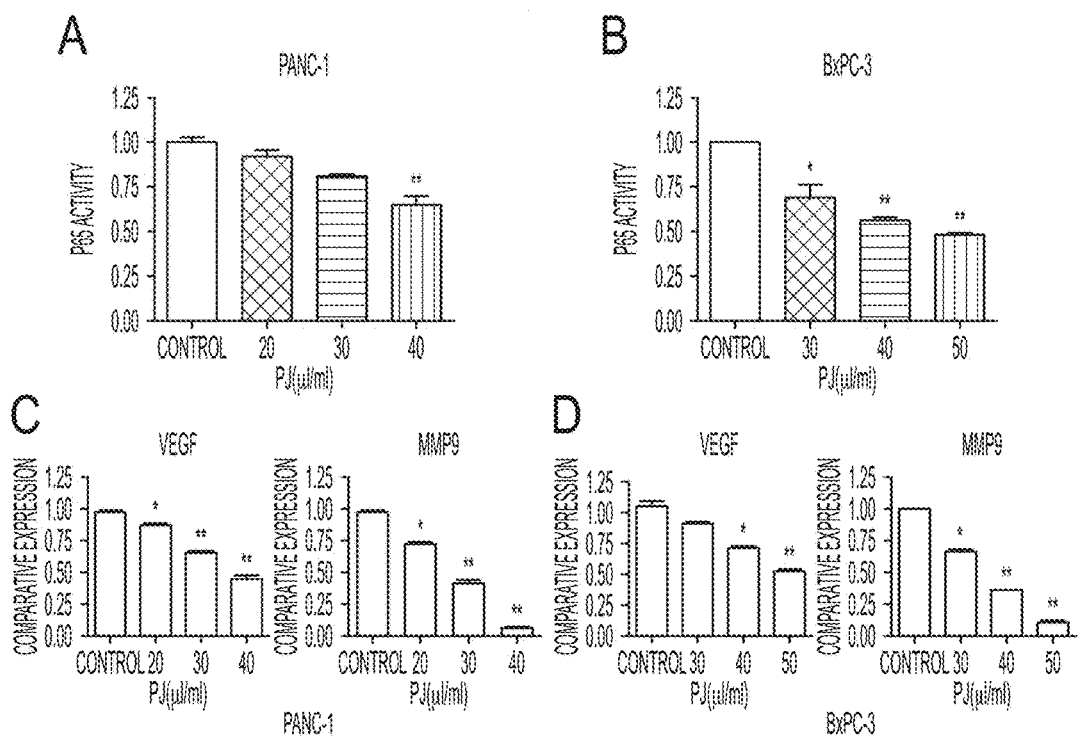
FIG. 5 shows the down regulation of NF-κB activity following PJ treatment in PANC-1 and BxPC-3 cells.

Microwell colorimetric NF-κB assay was performed to characterize the effect of PJ on NF-κB activity. FIG. 5 shows the down regulation of NF-κB activity as increasing concentration of PJ used in treatment on PANC-1 and BxPC-3 cells. FIGS. 5A and 5B shows the analysis of p65 activity in PANC-1 and BxPC-3. P65 activation decreased in a similar dose-dependent manner following PJ treatment in both cell lines. Both PANC-1 and BxPC-3 cell lines exhibited significantly lower NF-κB (p65) activity at higher concentrations of PJ used in treatment.

FIGS. 5C and 5D shows the effect of PJ on VEGF and MMP-9 expression in relative to DMSO treated control. VEGF and MMP-9 expression was significantly reduced in treatment with PJ at dose-dependent manner. The effect on MMP-9 was more pronounced in both cancer cell lines as observed in FIGS. 5C and 5D. Vascular endothelial growth factor (VEGF) and matrix metalloproteinase 9 (MMP9) being the downstream genes of NF-κB, are responsible for cancer cell invasion and migration expression. The expressions of VEGF and MMP9 were measured by real time PCR after reverse transcriptase PCR. These results strongly suggest that PJ inhibited NF-κB activity and its target genes expressions.

The results are presented as mean±SEM of three assay replicates. * indicates P<0.05 and ** indicates P<0.01 versus respective DMSO treated controls.

Inhibition of Cell Migration and Invasion by PJ

Figure 6:
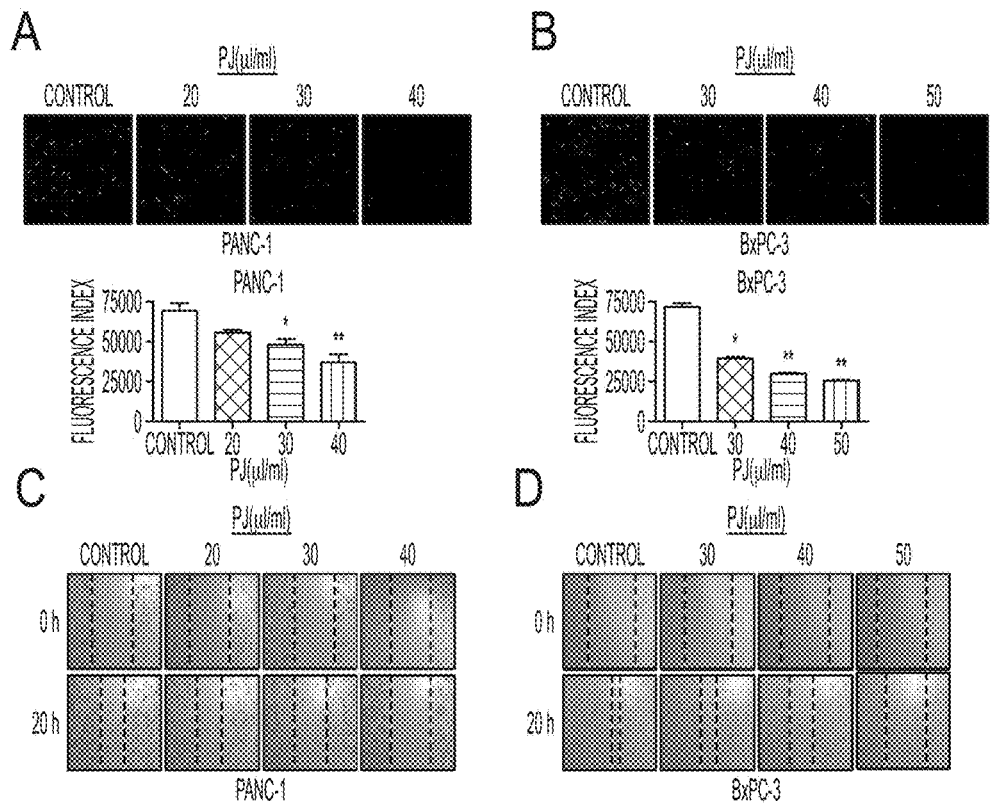
FIG. 6 shows the inhibition of cell invasion and migration in PANC-1 and BxPC-3 cell lines.

The cell invasion and wound healing assays were used to analyze the effect of PJ on invasion and migration on the pancreatic cancer cell lines. FIG. 6 show PJ inhibits migration and cell invasion in PANC-1 and BxPC-1 cell lines in dose-dependent manner. Cells were cultured in varying concentrations of PJ for 20 h and were photographed after staining with Calcein AM. Cells cultured in the absence of PJ are used as control. FIGS. 6A and 6B illustrates the fluorescence of the invaded cells in in PANC-1 and BxPC-1 cell lines respectively. PJ decreased cell invasion in a dose dependent manner, as semi-quantified by the fluorescence index reading. Results are presented as mean±SEM of three assay replicates. * indicates P<0.05 and ** indicates P<0.01 versus respective DMSO treated controls.

The wound healing assay shows the cell migration in PANC-1 and BxPC-1 cell lines as depicted in FIGS. 6C and 6D respectively. When the cells reached confluence, a single wound was scratched across each well. After 20 h incubation with various concentrations of PJ, wound closure areas were visualized using a microscope. These results support the cell invasion findings that increasing PJ concentrations prevents cell migration in an increased dose-dependent manner. Thus, this demonstrates that PJ effectively retards migration and metastasis in PANC-1 and BxPC-3.

Present invention discloses PJ which inhibits proliferation, growth, migration, and invasion by inducing apoptosis, cell cycle arrest, and down-regulating NF-κB activity in both cell lines.

This statement is supported by various experiments such as MTS and clonogenic assays wherein PJ inhibited cell proliferation and clonogenicity in both cell lines. Besides that, PJ was tested to be effective in inducing apoptosis in a dose-dependent manner for PANC-1 and BxPC-3. Furthermore, the flow cytometry analysis on cell cycle distribution revealed that PJ induces cell cycle arrest in the S phase for both PANC-1 and BxPC-3 cells. Together, these data suggest PJ inhibits cell growth, induces apoptosis and induces cell cycle arrest in these cancer cell lines and hence could prove to be an effective antitumor agent.

Western blot analysis evaluated the expression of caspases and PARP protein. The experiment data also demonstrated that PJ simultaneously caused a decrease in the expressions of the anti-apoptotic proteins such as Bcl-xL and Survivin in both PANC-1 and BxPC-3, and also increase in the expressions of pro-apoptotic proteins such as cleaved caspase 3, cleaved caspase 9 and cleaved PARP. Hence, present invention discloses that the apoptotic capacity of PJ is induced through a dual mechanism, demonstrating that PJ can indeed be a powerful nutraceutical against cancer.

NF-κB plays important roles in many cellular processes including cell proliferation, anti-apoptosis invasion, and angiogenesis all of which are crucial for cancer development and progression. By using the chemilluminance NF-κB ELISA kit, we demonstrated that P65 activity significantly decreased as PJ concentration increased in both cell lines as shown in FIGS. 5A and 5B. Since VEGF and MMP9 are known to be involved in downstream signaling of NF-κB responsible for cell migration and invasion, relative expressions of VEGF and MMP9 for both cell lines were evaluated. The study shows the expression of both VEGF and MMP9 was significantly decreased in response to increased PJ concentrations in both PANC-1 and BxPC-3 cell lines as shown in FIGS. 5C and 5D.

The extracts from oil palm disclosed in present invention have also exhibited properties to inhibit cell invasion and migration. The current studies show that PJ caused a dose-dependent reduction in cell invasion and migration in both PANC-1 and BxPC-3 cells as shown in FIG. 6. This further supports PJ's candidacy in treating cancer.

Thus, present invention has disclosed the extracts from oil palm to work as a multi-faceted chemotherapeutic agent against pancreatic cancer. Benefits of its consumption may potentially involve inhibition of cell proliferation and growth, and induction of cell cycle arrest and apoptosis. The mechanisms through which these actions occur have also been partially elucidated in this study, the most important of which is the evident down-regulation of the NF-κB pathway.

The composition as disclosed in present invention may be provided as compounds with pharmaceutically acceptable carriers. Present invention further discloses the use of therapeutically effective amount of a composition in the preparation of a medicament for preventing or inhibiting the growth of pancreatic cancer in an individual by administering to an individual in need thereof. The composition is accompanied with or without conventional chemotherapy or radiation therapy or surgery, or it may be administered orally or as a food supplement.

It is understood by a person skilled in the art that the methods for experiments and studies are described as exemplifications herein and thus the results are not intended, however, to limit or restrict the scope of the invention in any way and should not be construed as providing conditions, parameters, agents, chemicals or starting materials which must be utilized exclusively in order to practice the present invention. It is therefore understood that the invention may be practiced, within the scope of the appended claims, with equivalent methods for the experiments than as specifically described and stated in claims.

The invention claimed is:

1. A method for inhibiting proliferation or clonogenicity of a pancreatic cancer cell in an individual in need thereof, the method comprising administering a therapeutically effective amount of a composition comprising a plant extract to the individual in need thereof, wherein the plant extract is an oil palm extract.

2. The method of claim 1, wherein the administering is accompanied with conventional chemotherapy, radiation therapy or surgery.

3. The method of claim 1, wherein the composition is administered orally or as a food supplement.

4. The method of claim 1, wherein said plant extract is a water soluble, phenolic-rich extract.

5. The method of claim 1, wherein said pancreatic cancer cell is of a PANC-1 or a BxPC-3 cell line.

6. The method of claim 1, wherein said composition induces apoptosis.

7. The method of claim 1, wherein said composition regulates gene expression.

8. The method of claim 6, wherein said apoptosis is associated with inhibiting cell survival proteins.

9. The method of claim 6, wherein said apoptosis is associated with inhibiting anti-apoptotic protein.

10. The method of claim 9, wherein said antiapoptotic protein is Survivin.

11. The method of claim 7, wherein said gene expression regulated is associated with Bcl-2 family.

12. The method of claim 7, wherein said gene expression is associated with down-regulating Bcl-XL expression.

13. The method of claim 6, wherein said apoptosis is associated with increased expression of pro-apoptotic proteins.

14. The method of claim 13, wherein said proapoptotic proteins are cleaved caspase 3, caspase 9 or Poly (ADP-ribose) polymerase (PARP).

15. The method of claim 1, wherein said composition induces cell cycle arrest in S phase.

16. The method of claim 1, wherein said composition inhibits NF-κB activity.

17. The method of claim 16, wherein said NF-κB activity is inhibited via down-regulating p65 subunit activity.

18. The method of claim 17, wherein said downregulating is associated with decreasing vascular endothelial growth factor (VEGF) or matrix metalloproteinase 9 (MMP9) gene expression.

19. The method of claim 1, wherein said composition reduces cell invasion, cell migration or metastasis.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 1
cggagtgagt tgaaccag                                                 18

```
<210> SEQ ID NO 2
<211> LENGTH: 18
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 2
gtcccagtgg ggatttac                                                  18

<210> SEQ ID NO 3
<211> LENGTH: 20
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 3
gccttgcctt gctgctctac                                                20

<210> SEQ ID NO 4
<211> LENGTH: 20
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 4
ttctgccctc ctccttctgc                                                20

<210> SEQ ID NO 5
<211> LENGTH: 19
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 5
cagtgagctt cccgttcag                                                 19

<210> SEQ ID NO 6
<211> LENGTH: 20
<212> TYPE: DNA
<213> ORGANISM: Artificial Sequence
<220> FEATURE:
<223> OTHER INFORMATION: Primers used in real-time quantitative PCR of
      the human cancer cell lines PANC-1 and BxPC-3

<400> SEQUENCE: 6
acccagaaga ctgtggatgg                                                20
```